(12) United States Patent
Slangen

(10) Patent No.: US 6,397,494 B1
(45) Date of Patent: Jun. 4, 2002

(54) PROCESS FOR DRYING MELAMINE

(75) Inventor: Hubertus J. M. Slangen, Urmond (NL)

(73) Assignee: DSM N.V., Heerlen (NL)

( * ) Notice: Subject to any disclaimer, the term of this patent is extended or adjusted under 35 U.S.C. 154(b) by 0 days.

(21) Appl. No.: 09/680,455

(22) Filed: Oct. 6, 2000

Related U.S. Application Data

(63) Continuation of application No. PCT/NL99/00218, filed on Apr. 15, 1999.

(30) Foreign Application Priority Data

Apr. 17, 1998 (NL) .............................................. 1008912

(51) Int. Cl.⁷ .................................................. F26B 3/32
(52) U.S. Cl. ............................. 34/520; 34/519; 34/305; 544/200
(58) Field of Search .......................... 34/519, 520, 305; 544/203, 202, 201, 200; 528/129

(56) References Cited

U.S. PATENT DOCUMENTS

| | | | | |
|---|---|---|---|---|
| 4,239,739 A | * | 12/1980 | Sheridan et al. | 423/308 |
| 4,487,857 A | * | 12/1984 | Sugimori et al. | 523/335 |
| 5,202,438 A | * | 4/1993 | Paul | 544/198 |

FOREIGN PATENT DOCUMENTS

| WO | WO95/06042 | 3/1995 |
|---|---|---|

OTHER PUBLICATIONS

Ullmann's Encyclopedia of Industrial Chemistry, 1985, Fifth Edition, vol. B2, pp. 7.21–7.25.*
Chemical Engineer's Handbook, 1973, Fifth Edition, pp. 20.55–20.58.*
B. Elvers; Ullmann's Encyclopedia of Industrial Chemistry; Nelamine and Guanamines; Mar. 2, 1995; vol. A16.
The British Sulphur Corporation Limited; The manufacture of non–fertilizer nitrogen products; 1982; vol. 139, pp. 32–39.

* cited by examiner

Primary Examiner—Ira S. Lazarus
Assistant Examiner—Kathryn S. O'Malley
(74) Attorney, Agent, or Firm—Pillsbury Winthrop LLP

(57) ABSTRACT

The invention relates to a process for drying melamine wet cake to produce a dry melamine powder showing improved bulk properties, the drying being effected with a contact dryer. In particular the invention relates to a process for drying melamine wet cake that contains predominantly melamine crystals that have crystallized from a melamine solution in a crystallizer, the drying being effected with a contact dryer. The invention also relates to the drying of a melamine wet cake whose percentage of fines having a diameter of <21 $\mu$m is less than 30 wt. %, the drying being effected with a contact dryer.

7 Claims, No Drawings

PROCESS FOR DRYING MELAMINE

This is a Continuation of International Application No. PCT/NL99/00218 filed Apr. 15, 1999 which designated the U.S.

The invention relates to a process for drying melamine wet cake. In particular, the invention relates to a process for drying melamine wet cake which contains predominantly melamine crystals that are obtained from a concentrated melamine solution in a crystallizer. The invention particularly relates to a process for drying melamine wet cake containing less than 30 wt. % fines, the term fines being used herein to refer to particles having a diameter of less than 21 µm.

A variety of processes for the production of melamine are described in *Nitrogen,* No. 139, September/October 1982, pp. 31–39. A number of the disclosed processes produce, at an intermediate step, a slurry of melamine crystals and water. These slurries are then subjected to a variety of additional processing steps necessary to produce a dry melamine product.

One of the melamine processes described in Nitrogen was the Stamicarbon process. In the Stamicarbon process, a caustic solution is added to this slurry and the resulting mixture is heated to dissolve the melamine crystals to obtain a concentrate melamine solution. The melamine solution is then filtered to remove insoluble materials, such as catalyst particles, to obtain a purified melamine solution.

This purified melamine solution is then fed into a crystallizer operating at reduced temperature and pressure to crystallize the melamine. The crystallized melamine and the remaining solution form a slurry that is concentrated further using a cyclone. The concentrated slurry is then fed into a centrifuge where the melamine crystals are separated from most of the remaining solution. The resulting product is composes predominantly of wet melamine crystals that is commonly referred to as "wet cake" by persons skilled in the art.

Following the Stamicarbon process, the wet cake is then passed upwards through a vertical pipe using a stream of hot air to produce a dried melamine powder. This type of dryer will be referred to herein as a "flash dryer." below. The dried melamine powder and the hot air exiting the top of the flash dryer are then fed into a cyclone to separate the melamine powder. In addition to the Stamicarbon process described above, the Nitrogen article describes other processes in by which melamine wet cake may be obtained from the melamine slurry and subsequently dried.

The utility of the final dried melamine product is, however, related to more than simply the moisture content. Various bulk properties, in particular bulk density, compacted density, processing behaviour, and caking behaviour, are important factors reflecting a melamine product's transportability and processability. An object of the present invention is to provide a process that results in improved bulk properties. This object was achieved by drying the wet cake in a contact dryer instead of in a flash dryer. As used herein, the term "contact dryer" should be understood as referring to a dryer in which heat is applied to the wet cake predominantly via contact with the front surfaces, whether stationary and/or moving, of the contact dryer. The contact dryer surfaces are typically heated from the rear using a heating fluid such as steam or hot oil.

A number of types of drying apparatus, including tube bundle dryers, drum dryers, and tray dryers, can be configured as contact dryers in keeping with the present invention. A more detailed description of various contact dryers may be found in "Trocknungstechnik", by K. Kröll, Zweiter Band, Springer Verlag, 1978, pp. 364–73. Although a tube bundle dryer is preferred, the present invention is not so restricted and may be implemented with any suitable contact dryer.

According to the invention, the contact wall temperature in the contact dryer should be maintained at a temperature 100° C. and 220° C., preferably between 120° C. and 160° C. Drying processes utilizing wall temperatures below 100° C. are less effective, uneconomical, and should generally be avoided. Similarly, drying processes utilizing wall temperatures greater than 220° C. can produce unsatisfactory discolouration in the melamine.

Using a wall temperature of between 120° C. and 220° C., a residence time of between 0.1 and 10 hours, and preferably between 1 and 3 hours, is sufficient to dry melamine wet cake (moisture content of approximately 9 wt. % on a wet basis) to form a dry melamine powder (moisture content of less than 0.1 wt. % on a wet basis). As used herein, moisture content expressed in wt. % on a wet basis can expressed by the following formula using the weight of the remaining solvent ($W_s$) and the weight of the melamine ($W_m$):

$$[(W_s)/(W_s)+(W_m)]*100\%$$

Dried melamine powder, for example, will typically have a moisture content of less than 0.1 wt. % on a wet basis. Although as described with reference to melamine wet cake having a moisture content of about 9 wt. % in which the solvent is water, it will be appreciated that the present invention is not so limited. It is contemplated that the present invention may be used effectively on a range of wet cake compositions, moisture contents, and solvents.

The applicants have also found that the present invention decreases the production of melamine fines during the contact drying process, particularly when compared with the conventional flash drying process. Without being bound to any exact theory, it is assumed that the improvement in the bulk density, compacted density, processing behaviour and caking behaviour achieved with the present invention is at least partly due to the reduced formation of fines during the drying process.

The applicants demonstrated this reduced formation of fines in a series of experiments comparing the flash drying and contact drying processes. As produced by the Stamicarbon process, melamine wet cake usually contains less than 6 wt. % fines, in particular less than 4 wt. % fines, and more particularly, less than 2 wt. % fines. The initial fines content was evaluated by drying melamine wet cake, obtained using the Stamicarbon process, on a laboratory scale for 16 hours at a temperature of 150° C. As it may reasonably be assumed that no fines are formed during drying in the drying oven, it can be concluded that any increase in the number of fines results from the selected drying process.

When melamine wet cake produced via the Stamicarbon process having approximately 2 wt. % fines is dried with a flash dryer, the resulting dry melamine powder contains approximately 8 wt. % fines. This demonstrates that the number of fines increases dramatically during drying with a flash dryer.

Laser light diffraction, employing a Sympatec® Helos 12LA, was used for quantifying the percentage of fines present in the samples tested. The sample being tested was dispersed in air in a Rodos® dry feeder at a pressure of 20 mbar. In this case the melamine wet cake samples contained 9 wt. % moisture with the samples being dried to at least 0.1 wt. % moisture on a wet basis by the selected method. The reported moisture contents were determined by weighing a sample with Mettler® scales fitted with an LP16 heating element. After the initial weighing, the samples were heated and weighed again to determine the percentage of the original weight was lost due to evaporation of the solvent.

If, as the applicants suspect, the improvement in the bulk density, compacted density, processing behaviour, and caking behaviour possible through application of the present invention results from the reduced numbers of fines, the best results will be achieved with melamine wet cake having a sufficiently low initial level of fines. In those instances in which the initial level of fines is too high, restricting the formation of additional fines by using a contact dryer does not provide any great advantage. Without being bound to any scientific theory, the applicants believe that the manner in which the melamine crystals are formed effects the initial fines percentage in the wet cake.

The applicants have found that wet cake melamine having a low fines percentage can be obtained when the melamine crystals comprising the wet cake have predominantly and preferably crystallized from a melamine solution in a crystallizer. Drying such a wet cake with a contact dryer is particularly advantageous.

The melamine solution fed to the crystallizer may, however, contain some melamine crystals that were formed during earlier process steps. As a result, the final wet cake may contain a small portion of crystals that were not produced from the melamine solution in the crystallizer. It is preferred that the melamine crystals in a wet cake comprise at least 50 wt. %, and more preferably, 90 wt. %, melamine crystals formed from a melamine solution in a crystallizer. Examples of possible crystallizers are shown in "Perry's Chemical Engineers Handbook", by Don W. Green and James O. Maloney, 7th edition, Mc.Graw Hill, 1997, pages 18–44 to 18–55.

The Stamicarbon melamine production process described above is an example of a process that can produce a wet cake having a small amount of fines. It will be appreciated, however, that the invention is not restricted to drying a wet cake produced using the Stamicarbon process. It has been found that restricting the formation of fines by using a contact dryer instead of a flash dryer is advantageous when the percentage of fines in the wet cake is less than 30 wt. %, preferably less than 20 wt. %, more preferably less than 10 wt. %, and most preferably, less than 6 wt. %.

The invention will now be elucidated with reference to the following examples, without being limited hereto.

EXAMPLE 1

This example relates to the drying according to the invention of a melamine wet cake produced using the Stamicarbon process having a moisture content of 9 wt. % on a wet basis. The moisture content was determined according to the weighing method described above. A volume of 30 l of this wet cake was dried for 2 hours in a contact dryer, make Drais®, type T 50FM IG, volume 50. This is a contact dryer in which heating takes place via the wall. The wall temperature was 150° C. The dried product was then cooled in the dryer for 2 hours using a wall temperature of 20° C. The moisture content of the melamine powder dried according to this method was less than 0.1 wt. % on a wet basis. The settling angle, the bulk density, the compacted density, the settling angle, the caking behaviour and the percentage of fines of the resulting dry melamine powder were then determined. The percentage of fines in the wet cake was also determined.

EXAMPLE 2

This example relates to the drying according to the invention of melamine wet cake produced via the Stamicarbon process having a moisture content of 9 wt. % on a wet basis. A volume of 30 l of this wet cake was dried for 2.5 hours in the same way as in Example 1 and subsequently cooled in the same way and for the same length of time as in Example 1. The settling angle, the bulk density, the compacted density, the settling angle, the caking behaviour and the percentage of fines of the resulting dry melamine powder were then determined. The percentage of fines in the wet cake was also determined. The results are shown in Table 1.

Comparative Experiment

The bulk density, the compacted density, the settling angle, the caking behaviour and the percentage of fines of the normal plant product obtained by drying a wet cake produced via the Stamicarbon process on an industrial scale with a flash dryer were determined according to the methods mentioned in Examples 1 and 2. These product properties of the plant product were compared with the product properties of the products dried with the contact dryer according to Examples 1 and 2. The results of this comparison are shown in Table 1.

In evaluating the bulk properties of the melamine wet cake and dry melamine powder generated in the above experiments, the following procedures were utilized:

bulk density and compacted density were determined according to ASTM D 1895.

settling angle was determined according to ISO 4324. A smaller settling angle implies better processing behaviour.

caking behaviour was evaluated by storing the melamine for 3 days at a pressure of 600 kg/m$^2$. The size and hardness of the lumps consequently formed were visually assessed and served as a measure of the caking behaviour.

In addition, the percentages of fines in the melamine wet cake and in the dried powder melamine were determined. For the determination of the percentage of fines in the wet cake, the wet cake was dried in a drying oven according to the method described above, after which the percentage of fines was measured according to the laser diffraction method described above. The percentage of fines in the powder dried with the contact dryer was also measured according to the laser diffraction method described above.

Table 1 shows the results of the three experiments and measurements described above.

The following is apparent from Table 1: the bulk density of the melamine powder dried with the contact dryer is approximately 18% higher than the bulk density of the plant product. The compacted density of the melamine powder dried with the contact dryer is approximately 9% higher than the compacted density of the plant product. The melamine powder dried with the contact dryer has an average settling angle of 33°, whereas the plant product has a settling angle of 48°, which implies that the melamine powder dried with the contact dryer shows better processing behaviour. The caking tendency of the melamine powder dried with the contact dryer is lower than that of the plant product. The percentage of fines in the melamine powder dried with the contact dryer is 3.2–3.8 wt. %, whereas the percentage of fines in the plant product is 8 wt. %.

TABLE 1

| | drying time (hours) | bulk density (kg/m³) | Compacted density (kg/m³) | settling angle (°) | caking | % fines of <21 mm in wet cake | % fines of <21 mm in dried product |
|---|---|---|---|---|---|---|---|
| example 1 | 2 | 860 | 1100 | 32 | | 2.7 | 3.8 |
| example 2 | 2.5 | 860 | 1080 | 34 | Slight | 1.3 | 3.2 |
| comparative experiment (plant product, flash dryer) | | 730 | 1000 | 48 | Moderate | 2 | 8.0 |

What is claimed is:

1. Process for improving bulk properties of melamine, comprising drying melamine wet cake in a contact dryer at a wall temperature of from 100° C. to 220° C., whereby the percentage of fines having a particle size less than 21 µm in the dried melamine is less than 30 wt. %.

2. Process according to claim 1, wherein the percentage of fines of <21 µm in the wet cake is less than 20 wt. %.

3. Process according to claim 2, wherein the percentage of fines of <21 µm in the wet cake is less than 10 wt. %.

4. Process according to claim 3, wherein the percentage of fines of <21 µm in the wet cake is less than 6 wt. %.

5. Process according to claim 1, wherein the drying is effected with a tube bundle dryer.

6. Process according to any claims 1, wherein the drying takes place at a wall temperature of 120–160° C.

7. Process according to claim 1, wherein the drying time is 1–3 hours.

* * * * *